US008518028B2

(12) United States Patent
Brady et al.

(10) Patent No.: US 8,518,028 B2
(45) Date of Patent: Aug. 27, 2013

(54) METHODS FOR ENHANCING ACCOMMODATION OF A NATURAL LENS OF AN EYE

(75) Inventors: Daniel G Brady, San Juan Capistrano, CA (US); Rakhi Jain, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 737 days.

(21) Appl. No.: 12/570,780

(22) Filed: Sep. 30, 2009

(65) Prior Publication Data

US 2011/0077624 A1     Mar. 31, 2011

(51) Int. Cl.
*A61B 18/18*     (2006.01)
(52) U.S. Cl.
USPC ............................................................ 606/4
(58) Field of Classification Search
USPC .......................................... 606/4–6; 351/246
See application file for complete search history.

(56) References Cited

U.S. PATENT DOCUMENTS

| | | | |
|---|---|---|---|
| 4,559,942 A | 12/1985 | Eisenberg | |
| 4,764,930 A | 8/1988 | Bille et al. | |
| 5,225,858 A | 7/1993 | Portney | |
| 5,288,293 A | 2/1994 | O'donnell, Jr. | |
| 5,571,177 A | 11/1996 | Deacon et al. | |
| 5,713,892 A | 2/1998 | Shimmick | |
| 5,728,156 A | 3/1998 | Gupta et al. | |
| 5,984,962 A | 11/1999 | Anello et al. | |
| 5,993,438 A | 11/1999 | Juhasz et al. | |
| 6,210,005 B1 | 4/2001 | Portney | |
| 6,887,083 B2 | 5/2005 | Umeyama et al. | |
| 6,923,955 B2 | 8/2005 | Till et al. | |
| 7,044,945 B2 | 5/2006 | Sand | |
| 2001/0010019 A1 | 7/2001 | Schachar | |
| 2002/0103478 A1 | 8/2002 | Gwon et al. | |
| 2003/0028248 A1 | 2/2003 | Shahinpoor et al. | |
| 2004/0082993 A1 | 4/2004 | Woods | |
| 2004/0111153 A1 | 6/2004 | Woods et al. | |
| 2004/0199149 A1* | 10/2004 | Myers et al. .................... 606/4 |
| 2004/0243111 A1 | 12/2004 | Bendett et al. | |

(Continued)

FOREIGN PATENT DOCUMENTS

DE     102006036800 A1     2/2008
WO     WO0182815 A1     11/2001

(Continued)

OTHER PUBLICATIONS

International Search Report for Application No. PCT/US2010/050752, mailed on Mar. 3, 2011, 5 pages.

(Continued)

*Primary Examiner* — James Greece
(74) *Attorney, Agent, or Firm* — Abbott Medical Optics Inc.

(57) ABSTRACT

The accommodative properties of the natural lens of an eye, which tend to degrade with age, can be enhanced, restored, or otherwise improved using the in situ treatment techniques and methodologies provided here. One exemplary method of enhancing accommodative properties of the natural lens of an eye involves an initial step of specifying treatment areas of the natural lens. These treatment areas correspond to regions of the capsular bag or regions of the crystalline lens. The method continues by increasing stiffness of the treatment areas while all or portions of the natural lens remains in situ. This results in stiffened areas of the natural lens that enhance transfer of ciliary muscle forces to a center region of the crystalline lens.

27 Claims, 8 Drawing Sheets

(56) References Cited

U.S. PATENT DOCUMENTS

| | | |
|---|---|---|
| 2006/0253196 A1 | 11/2006 | Woods |
| 2006/0265058 A1 | 11/2006 | Silvestrini |
| 2007/0185475 A1 | 8/2007 | Frey et al. |
| 2008/0140192 A1 | 6/2008 | Humayun et al. |
| 2008/0161913 A1 | 7/2008 | Brady et al. |
| 2008/0161914 A1 | 7/2008 | Brady et al. |
| 2010/0292678 A1 | 11/2010 | Frey et al. |

FOREIGN PATENT DOCUMENTS

| | | |
|---|---|---|
| WO | WO02071976 A2 | 9/2002 |
| WO | WO03057081 A2 | 7/2003 |
| WO | WO2004039395 A1 | 5/2004 |
| WO | WO2004082542 A2 | 9/2004 |
| WO | WO2007084602 A2 | 7/2007 |
| WO | WO2010059847 A1 | 5/2010 |

OTHER PUBLICATIONS

Pandey et al., "Creating cataracts of varying hardness to practice extracapsular cataract extraction and phacoemulsification" Journal of Cataract & Refractive Surgery, vol. 26, pp. 322-329(2000).

Pau, "Cortical and Subcapsular Cataracts: Significance of Physical Forces" Ophthalmologica, vol. 220 pp. 1-5(2006).

Hovanesian, "Cataract wound closure with a ploymerizing liquid hydrogel ocular bandage" Journal of Cataract & Refractive Surgery, vol. 35 pp. 912-916(2009).

Hovanesian et al., "Watertight cataract incision closure using fibrin tissue adhesive" Journal of Cataract & Refractive Surgery, vol. 33, pp. 1461-1463(2007).

Menabuoni et al., "Laser-assisted corneal welding in cataract surgery: Retrospective study" Journal of Cataract & Refractive Surgery, vol. 33, pp. 1608-1612(2007).

Chan et al., "Effect of photochemical crosslinking on the microstructure of collagen and a feasibility study on controlled protein release" Acta Biomaterialia, pp. 1627-1636(2008).

Tseng et al., "How actin crosslinking and bundling proteins cooperate to generate an enhanced cell mechanical response" Biochemical and Biophysical Research Communications 334 pp. 183-192(2005).

Sugiura et al., "Creating cataract in a pig eye" Journal of Cataract & Refractive Surgery, vol. 25 pp. 615-621(1999).

Shentu et al., "Combined microwave energy and fixative agent for catarat induction in pig eyes", Journal of Cataract & Refractive Surgery, vol. 35 pp. 1150-1155(2009).

Pandey et al., "Induction of Cataract of varying degrees of hardness in human eyes obtained postmortem for Cataract Surgeon Training", Induction of Hard Nuclear Cataracts, vol. 129, No. 4 pp. 557-558(2000).

Henderson, et al., "Stepwise approach to establishing an ophthalmology wet laboratory", Journal of Cataract Refractive Surgery, vol. 35 pp. 1121-1128(2009).

Ayaki et al., "Histopathologic study of after cataract in the pseudophakic rabbit eye using out-of-the-bag fixation, ," Nippon Ganka Gakkai Zasshi, pp. 553-558, 1990, vol. 94 (6).

Ayaki et al, "Histopathologic study of after-cataract in the pseudophakic rabbit eye using in-the-bag fixation, ," Nippon Ganka Gakkai Zasshi , pp. 559-565, 1990, vol. 94 (6).

Biedner B., et al., "Subconjunctival Dislocation of Intraocular Lens Implant," American Journal of Opthamology, 1977, vol. 84 (2), pp. 265-266.

Bloom S.M., et al., "Scleral Fixation Suture for Dislocated Posterior Chamber Intraocular Lens," Ophthalmic Surgery, 1990, vol. 21 (12), pp. 851-854.

Bowman C.B., et al., "Noninvasive Repositioning of a Posterior Chamber Intraocular Lens Following Pupillary Capture," Journal of Cataract and Refractive Surgery, 1991, vol. 17 (6), pp. 843-847.

Chan C.K., "An Improved Technique for Management of Dislocated Posterior Chamber Implants," Ophthalmology, 1992, vol. 99 (1), pp. 51-57.

Corcoran M.F., et al., "Spontaneous Repositioning of a Dislocated Medallion Intraocular Lens," Journal of the American Intra-Ocular Implant Society, 1985, vol. 11 (6), pp. 598-599.

Flynn H.R., et al., "Management of Subluxated and Posteriorly Dislocated Intraocular Lenses Using Pars Plana Vitrectomy Instrumentation," Journal of Cataract and Refractive Surgery, 1990, vol. 16 (1), pp. 51-56.

Glasser A., "Accommodation" in: Encyclopedia of Eye, vol. 1, Dartt D.A., ed., Oxford Academic Press, 2010, pp. 8-17.

Glasser A., et al., "Accommodation and Presbyopia" in: Adler's Physiology of the Eye, 10th Edition, Kaufman P.L., et al., Eds., Mosby, 2002, pp. 195-233.

Glasser A., "Physiology of Accommodation and Presbyopia" in: Surgery for Hyperopia, Sher N.A., Ed., Slack, Inc., 2004, pp. 11-21.

Glasser A., "The Helmholtz Mechanism of Accommodation" in: Hyperopia and Presbyopia, Chapter 3, Tsubota K., et al., eds., Marcel Dekker, Inc., 2003, pp. 27-47.

International Preliminary Report on Patentability and Written Opinion for Application No. PCT/US2010/050752, mailed on Apr. 3, 2012, 9 pages.

International Search Report and Written Opinion for Application No. PCT/US2012/028095, mailed on Jun. 19, 2012, 11 pages.

Moretsky S.L., "Suture Fixation Technique for Subluxated Posterior Chamber IOL through Stab Wound Incision," Journal of the American Intra-Ocular Implant Society, 1984, vol. 10 (4), pp. 477-480.

Nabors G., et al., "Ciliary Sulcus Suturing of a Posterior Chamber Intraocular Lens," Ophthalmic Surgery, 1990, vol. 21 (4), pp. 263-265.

Neumann A.C., et al., "Complications Associated with STAAR Silicone Implants," Journal of Cataract and Refractive Surgery, 1987, vol. 13 (6), pp. 653-656.

Nevyas H.J., et al., "A YAG Laser Technique to Facilitate Removal of Posterior Chamber Intraocular Lenses from the Capsular Bag," Journal of Cataract and Refractive Surgery, 1987, vol. 13 (2), pp. 201-204.

Poley B.J., et al., "A Closed Technique for Repositioning Dislocated Iris Plane Lenses," Journal of the American Intra-Ocular Implant Society, 1979, vol. 5 (4), pp. 316-320.

Praeger D.L., "Praeger Micro Irrigating Hook Intraocular Lens Implantation," Ophthalmic Surgery, 1979, vol. 10 (7), pp. 30-32.

Ripken T., et al., "Fs-Laser Induced Elasticity Changes to Improve Presbyopic Lens Accommodation," Graefe's Archive for Clinical and Experimental Ophthalmology, 2008, vol. 246 (6), pp. 897-906.

Smiddy W.E., "Dislocated Posterior Chamber Intraocular Lens: A New Technique of Management," Archives of Ophthalmology, 1989, vol. 107 (11), pp. 1678-1680.

Smiddy W.E., et al., "Management of Dislocated Posterior Chamber Intraocular Lenses," Ophthalmology, 1991, vol. 98 (6), pp. 889-894.

Stark W.J., et al., "Management of Posteriorally Dislocated Intraocular Lenses," Ophthalmic Surgery, 1980, vol. 11 (8), pp. 495-497.

Wand M., et al., "Thymoxamine Hydrochloride:An Alpha-adrenergic Blocker," Survey of Ophthalmology, 1980, vol. 25 (2), pp. 75-84.

Webber H.A., et al., "The Role of the Capsular Bag in Accommodation" in: Current Aspects of Human Accommodation II, Guthoff R., eds., Heidelberg, Kaden Verlag, 2003, pp. 119-126.

* cited by examiner

FIG. 11 too long subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may also be used in the following description for the purpose of reference only, and thus are not intended to be limiting. For example, terms such as "upper", "lower", "anterior", "posterior", "inner", and "outer" may refer to directions in the drawings to which reference is made and/or the orientation or location of portions of the component within a consistent but arbitrary frame of reference which is made clear by reference to the text and the associated drawings describing the component under discussion. Such terminology may include the words specifically mentioned above, derivatives thereof, and words of similar import.

The techniques, devices, methodologies, and procedures described herein may be utilized to enhance the accommodative properties and characteristics of a natural lens of an eye. These procedures modify or otherwise physically transform one or more components of the natural lens while it remains in situ. Moreover, the disclosed treatment methods are generally minimally invasive. Although the techniques and technologies described here are particularly suitable to treat presbyopia, they could also be utilized to treat other conditions or diseases of the eye (including, without limitation: hyperopia, myopia, or optical aberrations of the eye or cornea such as spherical aberrations, coma, or astigmatism). Indeed, the in situ natural lens treatment procedures described here could be suitably modified to treat one or more of these conditions in any combination. When used to treat presbyopia, these procedures can restore at least some of the accommodative characteristics of the natural lens such that the patient need not wear reading glasses or use corrective lenses.

Figure 1:
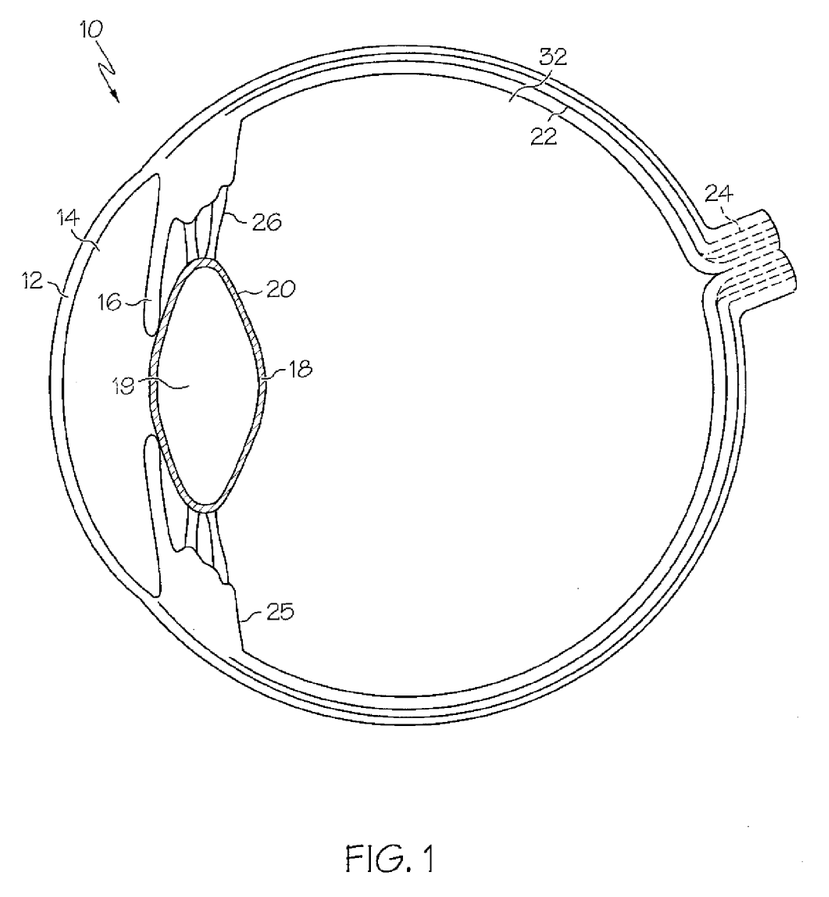

FIG. 1 is a cross-sectional diagram of a human eye 10. Light enters from the left of FIG. 1, passes through the cornea 12, the anterior chamber 14, and the iris 16, and enters the capsular bag 18. The crystalline lens 19 is located inside the capsular bag 18, and the crystalline lens 19 occupies essentially the entire interior of the capsular bag 18. After passing through the crystalline lens 19, light exits the posterior wall 20 of the capsular bag 18, passes through the posterior chamber 32, and strikes the retina 22, which detects the light and converts it to a signal transmitted through the optic nerve 24 to the brain.

As used in this specification, a "natural lens" of an eye includes at least two components: a capsular bag and a crystalline lens that resides within the capsular bag. Accordingly, modification, treatment, or transformation of the natural lens may be associated with physical changes made to the capsular bag alone, the crystalline lens alone, or both the capsular bag and the crystalline lens. Moreover, this specification refers to in situ treatment of the natural lens; as used here, a component of the natural lens is considered to be "in situ" if all or portions of the natural lens remain in the eye during the treatment procedure. In accordance with some treatment methods, the natural lens remains intact, or largely intact, and in situ during the treatment procedure. In some embodiments, the crystalline lens is partially or entirely removed, wherein a treatment procedure is performed on remaining portions of the natural lens, for example, on all or portions of the capsular bag.

A normal or well-corrected eye forms an image at the retina 22. If the natural lens has too much or too little power, the image shifts axially along the optical axis away from the retina 22, toward or away from the natural lens. Note that the power required to focus on a close or near object is greater than the power required to focus on a distant or far object. The difference between the "near" and "far" powers is usually referred to as the range of accommodation. As used herein, the term "near power" means an add power of at least one diopter (typically at least two or three diopters).

The capsular bag 18 is acted upon by the ciliary muscle 25 via the zonules 26, which distort the anterior surface of the capsular bag 18 by stretching it radially in a relatively thick band about its equator. Empirical data shows that the ciliary muscle 25 and/or the zonules 26 typically exert a total ocular force, which is distributed generally uniformly around the equator of the capsular bag 18. Although the range of ocular force may vary from patient to patient, it should be noted that for each patient, the range of accommodation is limited by the total ocular force that can be exerted. Consequently, it is desirable to have a relatively large change in power for relatively low ciliary muscle forces.

When the eye 10 focuses on a relatively close object, as depicted in FIG. 1, the zonules 26 relax and the capsular bag 18 returns to its natural shape in which it is relatively thick at its center and has more steeply curved sides. As a result of this action, the power of the crystalline lens 19 increases (i.e., one or both of the radii of curvature can decrease, and/or the crystalline lens 19 can become thicker, and/or the crystalline lens 19 may also move axially), placing the image of the relatively close object at the retina 22. If the crystalline lens 19 does not accommodate well (due to, for example, presbyopia), then the image of the relatively close object would be located behind the retina 22, and the image would appear blurred.

To focus on a distant object, the ciliary muscle 25 relaxes and the zonules 26 are stretched to change the shape of the capsular bag 18, which becomes thinner at its center and has less steeply curved sides (relative to that shown in FIG. 1). Thus, the outward radial pulling forces reduce the power of the crystalline lens 19 by flattening (i.e., lengthening radii of curvature and/or thinning) the crystalline lens 19, placing the image of the relatively distant object at the retina 22.

Figure 2:
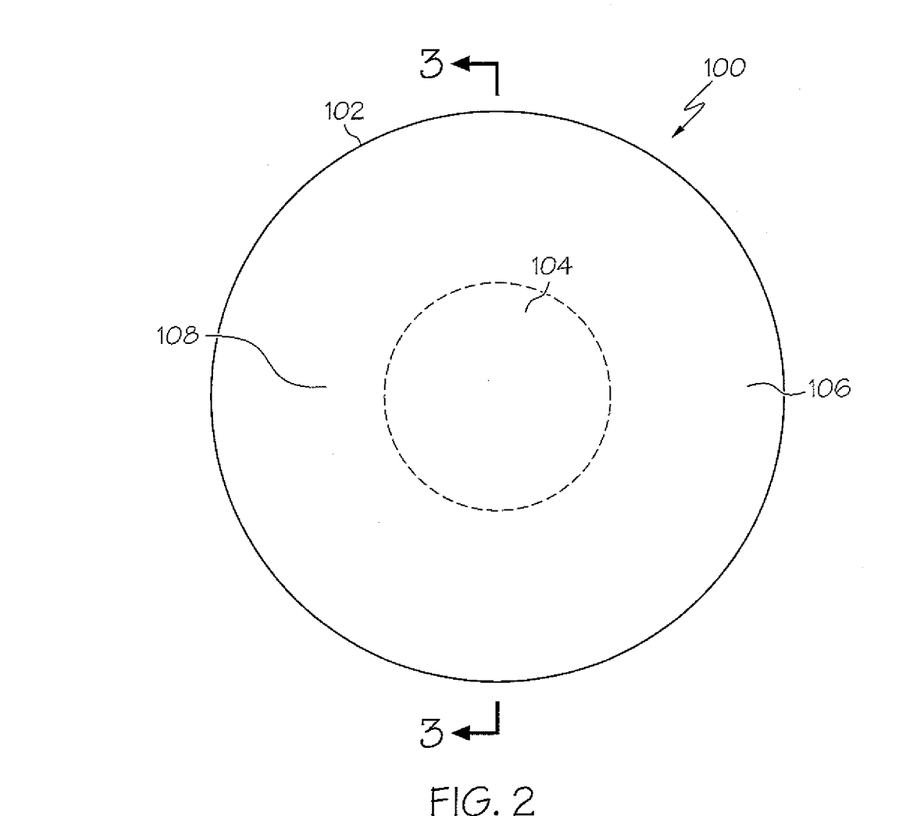
Figure 3:
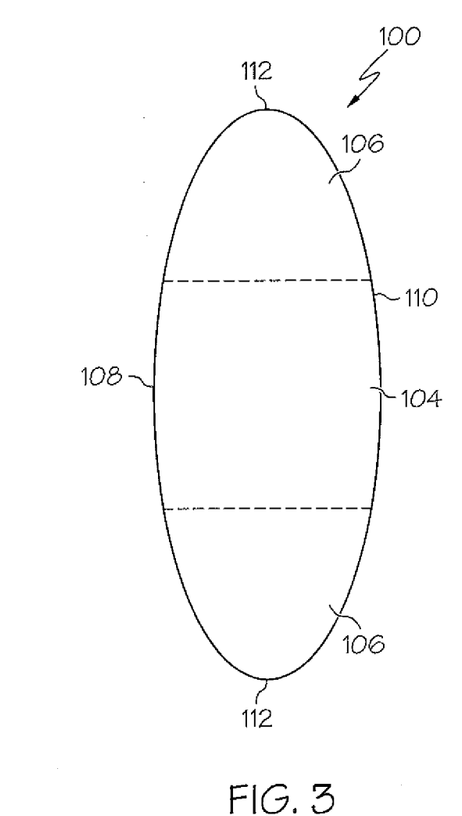

FIG. 2 is a front view of a crystalline lens 100 of a human eye, and FIG. 3 is a cross-sectional view of the crystalline lens 100 as viewed from line 3-3 in FIG. 2. For simplicity and ease of description, the crystalline lens 100 is depicted with a circular perimeter 102 when viewed along the optical axis (FIG. 2). In reality, the crystalline lens 100 will not generally have a perfectly circular boundary and, indeed, the shape of the boundary will change with accommodation. For simplicity and ease of description, the crystalline lens 100 is depicted with an elliptical cross-section or side profile (FIG. 3). In reality, the side profile and boundary of the crystalline lens will not generally be perfectly elliptical and, indeed, the shape of the side profile and boundary will change with accommodation. The specific shapes and profiles shown in the figures are merely illustrative, and are not intended to restrict or limit the described subject matter in any way.

The crystalline lens 100 generally includes a center region 104 and a peripheral region 106 outside the center region 104. The dashed lines in FIG. 2 and FIG. 3 represent an imaginary perimeter or boundary of the center region 104. The actual dimensions of the center region 104 and the peripheral region 106 will vary from one person to another. If, for example, the crystalline lens 100 has a diameter of about ten millimeters, then the center region 104 might have a diameter of about two to six millimeters (although these measurements will vary from one person to another). The optical power of the center region 104 is more sensitive to changes in ciliary muscle forces, relative to the optical power of the peripheral region 106. Thus, the center region 104 contributes more to optical power change for a given ciliary muscle force, relative to the contribution of the peripheral region 106.

The crystalline lens 100 has an anterior surface 108, a posterior surface 110, and an equator 112 that separates the anterior surface 108 from the posterior surface 110. For the illustrated crystalline lens 100, the equator 112 corresponds to the circular perimeter 102 shown in FIG. 2. As shown in FIG. 3, the anterior surface 108 may include some of the peripheral region 106 and some of the center region 104. Similarly, the posterior surface 110 may include some of the peripheral region 106 and some of the center region 104.

As the crystalline lens of an eye ages, it tends to harden or stiffen, which results in accommodation loss. In addition, the axial thickness of the crystalline lens has been shown to increase with age, that is, become thicker. In other words, as the crystalline lens ages, the same amount of ciliary muscle force may become less and less effective at altering the shape of the crystalline lens. Furthermore, studies have shown that the center region 104 hardens with age at a higher rate than the peripheral region 106. The techniques described here physically manipulate and transform the crystalline or natural lens while it remains in situ to enhance, restore, or otherwise improve its accommodative properties. In certain embodiments, the natural lens is treated in a way that leaves the center region 104 in its previous condition (or substantially in its previous condition). In other words, the optically sensitive center region 104 need not be transformed, modified, or invaded and, in some embodiments, the physical transformation is restricted to the peripheral region 106. As explained in further detail below, the natural lens is treated to increase its stiffness in certain regions or areas and in such a way that enhances the transfer of ciliary muscle forces to the center region of the crystalline lens. Unless noted otherwise, this specification uses the words "stiffness" and "stiffen" in a generalized manner that also encompasses and includes other words and phrases in the fields of material science, chemistry, dynamics, etc. In this regard, "stiffness" may include or contemplate any of the following terms, without limitation: hardness; modulus of elasticity; a ratio of applied force to displacement caused by the applied force; resilience; a ratio of applied force to optical power change; etc.

Figure 4:
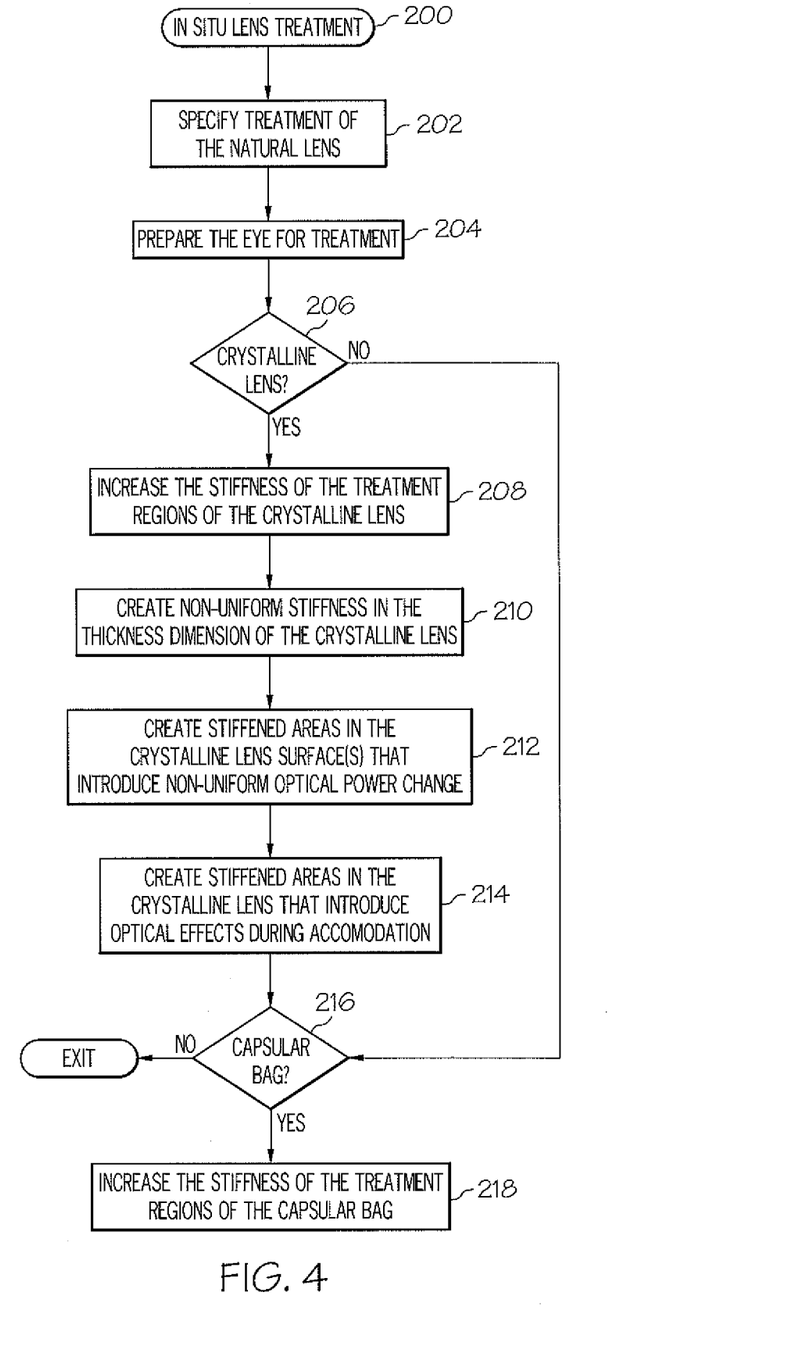

FIG. 4 is a flow chart that illustrates an exemplary embodiment of an in situ lens treatment process 200. It should be appreciated that the lens treatment process 200 may include any number of additional or alternative tasks, the tasks shown in FIG. 4 need not be performed in the illustrated order, and that the lens treatment process 200 may be incorporated into a more comprehensive procedure or process having additional tasks that are not described in detail herein. Moreover, one or more of the illustrated tasks of the lens treatment process 200 may be optional in nature and, therefore, such optional tasks could be omitted.

The lens treatment process 200 represents an exemplary method of enhancing the accommodative or other properties of a natural or crystalline lens of an eye, where the natural lens mechanically responds to ciliary muscle forces. The lens treatment process 200 assumes that the eye undergoing treatment has lost at least some of its ability to effectively and efficiently accommodate under normal ciliary muscle forces. The lens treatment process 200 may begin by identifying and/or specifying or designating certain treatment areas of the natural lens (task 202). For this embodiment, the specified treatment areas might correspond to treatment regions of the natural lens, including treatment of regions of the capsular bag and/or treatment regions of the crystalline lens. The specified treatment areas represent regions, volumes, sections, spaces, and/or surfaces that will be stiffened by the lens treatment process 200. The particular layout, topology, pattern, or configuration of the treatment areas can vary to suit the needs of the patient. For certain situations, task 202 specifies treatment areas that correspond to peripheral regions of the crystalline lens. Alternatively (or additionally), task 202 might specify treatment areas that correspond to peripheral regions of the capsular bag. Moreover, the amount by which a specified treatment area is stiffened might vary from one patient to another and/or from one eye to another. Furthermore, whether the capsular bag or the crystalline lens (or both) is stiffened could be determined in advance by the surgeon or ophthalmologist.

After planning and specifying the desired treatment areas, the patient and the eye can be prepared for the treatment procedure (task 204). The lens treatment process 200 is performed while all or portions of the natural lens remains in situ. Thus, it may be desirable or necessary to sedate or anesthetize the patient. It may also be desirable or necessary to dilate the pupil of the eye undergoing treatment to provide line-of-sight access to the treatment areas of the natural lens. It may also be desirable or necessary to clamp the eyelid open, to immobilize the eye undergoing treatment, and/or take other measures that facilitate a safe and effective procedure. Task 204 is also associated with the preparation of the equipment, devices, chemical agents, compounds and/or other items that might be needed to actually perform the treatment procedure. These items will become apparent from the following description.

The illustrated embodiment of the lens treatment process 200 contemplates the possibility of treating the capsular bag only, the crystalline lens only, or both the capsular bag and the crystalline lens. Thus, if the crystalline lens is to be treated (query task 206), then the lens treatment process 200 continues by increasing the stiffness of designated treatment regions of the crystalline lens (task 208). Notably, task 208 is performed while all or portions of the natural lens remains in situ, and in a manner that results in stiffened areas of the crystalline lens that enhance transfer of ciliary muscle forces to the center region of the crystalline lens. Although "increasing the stiffness" is mentioned here, task 208 could alternatively or additionally be associated with increasing the hardness of the designated treatment regions of the crystalline lens and/or increasing the modulus of elasticity of the designated treatment regions of the crystalline lens.

Figure 5:
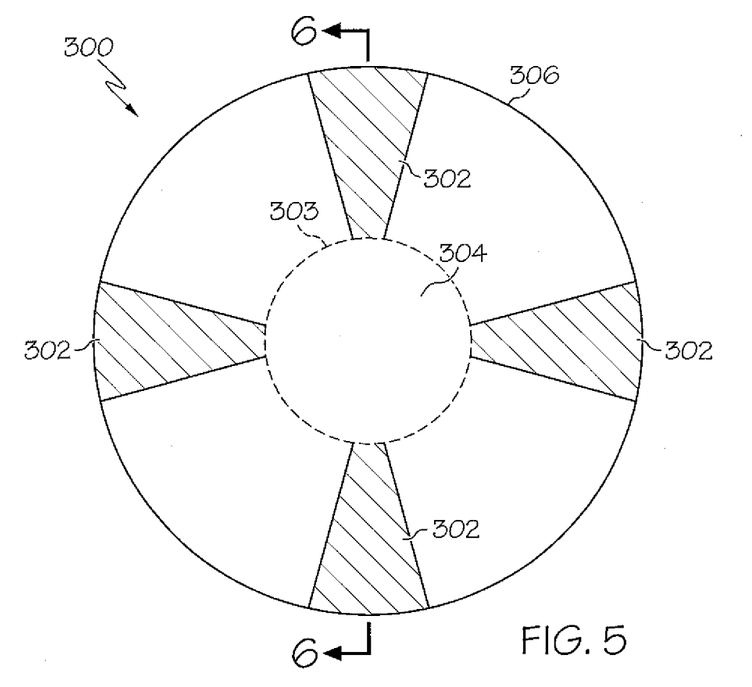

In certain embodiments, the lens treatment process 200 is utilized to stiffen peripheral regions of the crystalline lens. This creates stiffened areas of the crystalline lens that generally facilitate effective and efficient transfer of ciliary muscle forces from the peripheral region of the crystalline lens to the center region of the crystalline lens. In practice, task 208 is performed to increase the stiffness of the peripheral regions of the crystalline lens in accordance with a predetermined stiffening pattern, layout, or plan (e.g., the specified treatment areas designated during task 202). In this regard, FIG. 5 is a front view of a crystalline lens 300 of a human eye after an in situ accommodation enhancement procedure. The cross-hatched regions of the crystalline lens 300 represent the stiffened treatment areas. This particular crystalline lens 300 includes a stiffening pattern that defines a plurality of radial stiffening spokes, segments, arms, or regions 302 for the peripheral regions of the crystalline lens 300. Although not required, the four spokes 302 in this embodiment are all about the same shape and size, and the four spokes 302 form a substantially symmetrical stiffening pattern. Each of the spokes 302 runs longitudinally between the imaginary boundary 303 of the center region 304 of the crystalline lens 300 and the outer circular perimeter 306 of the crystalline lens 300. Alternatively, one of more of the spokes 302 could terminate before the imaginary boundary 303 and/or before the circular perimeter 306.

The shape, size, number, dimensions (e.g., width, length, depth or thickness, area, height) and/or arrangement of stiffening spokes or regions 302 can vary from one crystalline lens to another, and these defining characteristics of the stiffening pattern can be determined to suit the needs of the patient. Moreover, stiffening spokes or other stiffening features could be arranged in a regular pattern around the crystalline lens (as depicted in FIG. 5), or they may be arranged such that they only reside in certain regions of the crystalline lens (e.g., stiffening features may be located only in the top half, bottom half, left half, right half, or any divided segment of the crystalline lens). Although not shown, certain embodiments could employ continuous bands or rings around the center region of the crystalline lens and/or around any arbitrary point defined on the crystalline lens. For example, a crystalline lens may be treated to form one or more 360-degree stiffening bands, which may, but need not, have varying degrees of stiffness.

It should be appreciated that any arrangement of stiffening elements, features, and/or shapes could be created, and that the formation of spokes as shown in FIG. 5 is merely one exemplary result. For example, a crystalline lens could be treated to form any number of discrete "blocks" or "islands" that represent the stiffened features. Such stiffening blocks or islands may be uniformly or non-uniformly shaped, uniformly or non-uniformly sized, arranged in a regular or irregular pattern, arranged in a repeating or non-repeating pattern, randomly arranged, etc. Consequently, any number of individual stiffening features can be formed in a crystalline lens, with adjacent or surrounding non-stiffened (or softened) areas or sections of the crystalline lens.

Moreover, it may be desirable to form stiffening features (such as spokes) that have anisotropic stiffening characteristics. In other words, it may be desirable to stiffen a crystalline lens primarily or only in the radial dimension, without stiffening it in the circumferential and/or axial dimensions. In this regard, the crystalline lens is treated such that the stiffening effect is biased in one or more designated directions, dimensions, or orientations. Anisotropic or directional stiffening of a crystalline lens could be obtained by an appropriate design, configuration, and arrangement of stiffening features, and/or by using appropriate stiffening techniques (described in more detail herein).

Figure 6A:
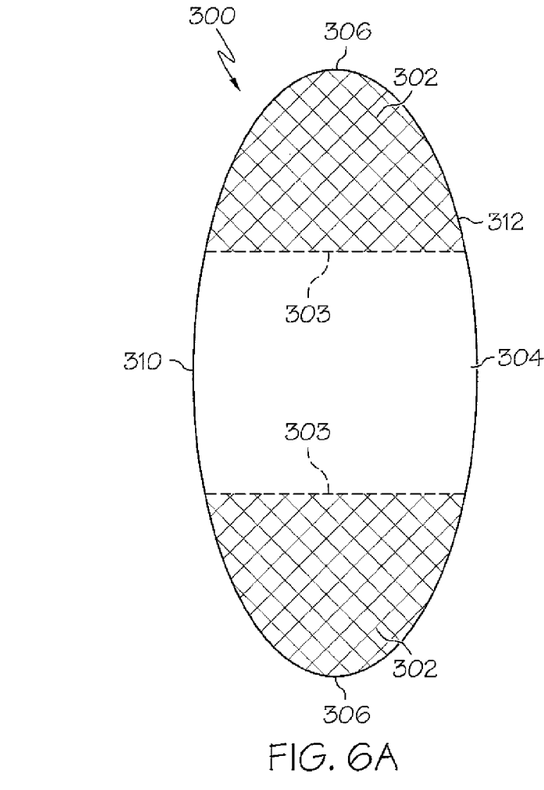

The cross-sectional profile of the stiffened regions may also be controlled to enhance accommodation in the desired manner. In this regard, FIG. 6A depicts a cross-sectional view of the crystalline lens 300 as viewed from line 6-6 in FIG. 5. FIG. 6A illustrates one scenario where the properties and characteristics of the spokes 302 are substantially consistent and uniform throughout the cross-sectional profile of the stiffened treatment areas. The consistent cross-hatching used in FIG. 6A represents the virtually uniform and consistent stiffness profile between the anterior surface region 310 and the posterior surface region of the crystalline lens 300.

Figure 6B:
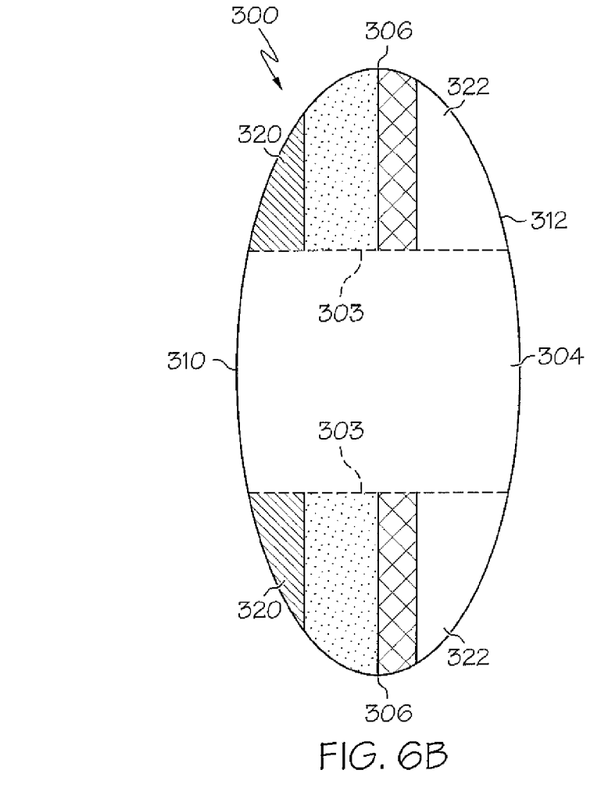

Referring again to FIG. 4, the lens treatment process 200 could be optionally utilized to create non-uniform stiffness in the thickness dimension of the crystalline lens (task 210). In this regard, FIG. 6B depicts a cross sectional view of an alternate version of the crystalline lens 300. In this version, the treatment procedure has created a non-uniform stiffness profile between the anterior surface region 310 and the posterior surface region of the crystalline lens 300. The illustrated embodiment includes four different "slices" that each represent different stiffness properties for the crystalline lens 300, although any number of slices could be realized. For example, the anterior slice 320 may have a first average modulus of elasticity, the posterior slice 322 may have a second average modulus of elasticity, and so on. Such a non-uniform stiffness profile may be desirable to customize the mechanical response of the treated crystalline lens in the presence of ciliary muscle forces. In accordance with certain implementations, the treatment procedure creates a stiffness gradient between the anterior surface region 310 and the posterior surface region 312 of the crystalline lens 300. In other words, the stiffness of a spoke 302 may increase or decrease (monotonically or strictly) in the thickness dimension of the crystalline lens 300. Similarly, the stiffness of a spoke 302 may change in the radial dimension, the angular or circumferential dimension, and/or in any designated dimension.

The lens treatment process 200 could also be used to create stiffened areas that are arranged and oriented to introduce non-uniform optical power change for the anterior and posterior surfaces of the crystalline lens during accommodation (task 212). In this regard, the crystalline lens could be stiffened such that the anterior surface of the crystalline lens deforms more or less relative to the posterior surface. Such a non-uniform response to ciliary muscle forces may be desirable in some patients. As yet another option, the lens treatment process 200 could be executed to create stiffened areas that are arranged and oriented to introduce certain optical effects during accommodation (task 214). Thus, the stiffened areas can be customized and oriented to produce optical effects that are intended to at least partially correct or compensate for common vision conditions. Accordingly, task 214 can be controlled to introduce one or more of the following optical effects, without limitation: lens power; spherical aberration; multifocality (provide a plurality of different focal lengths); coma; astigmatism; or higher order aberrations.

Figure 7:
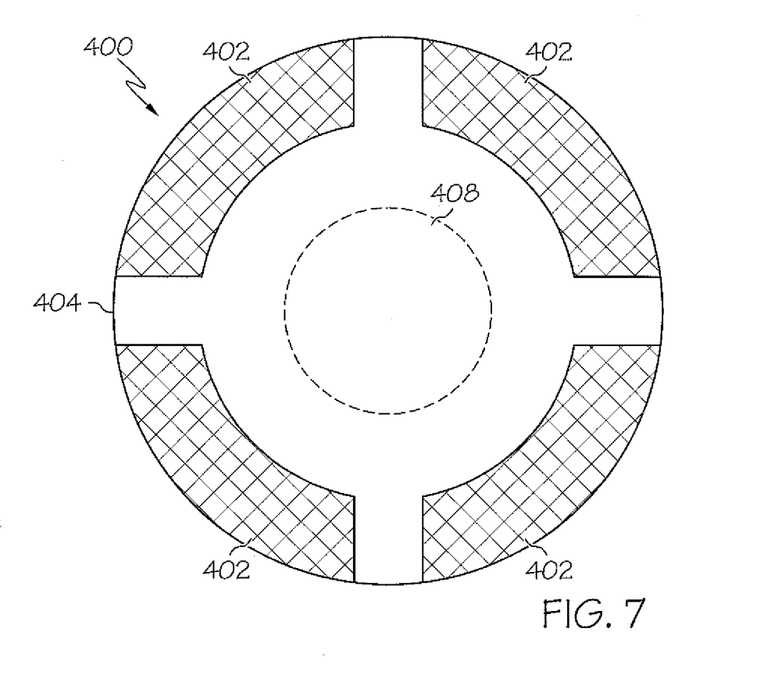
Figure 8:
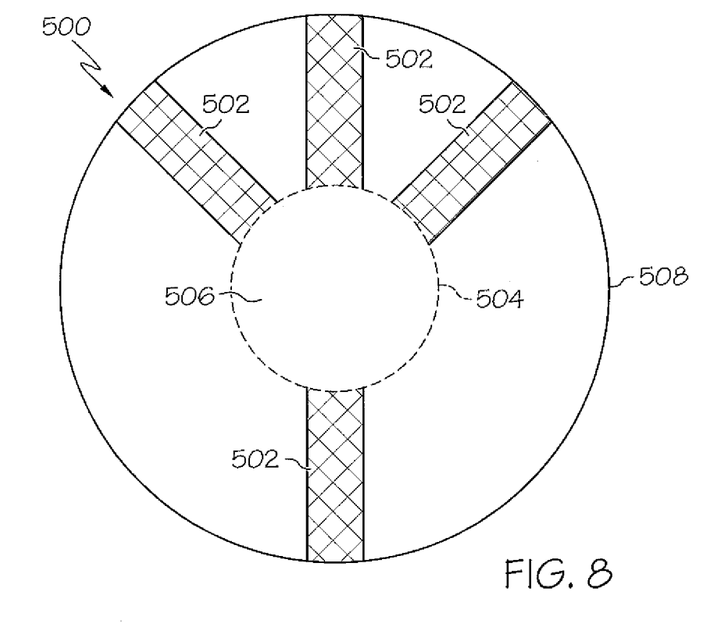
Figure 9:
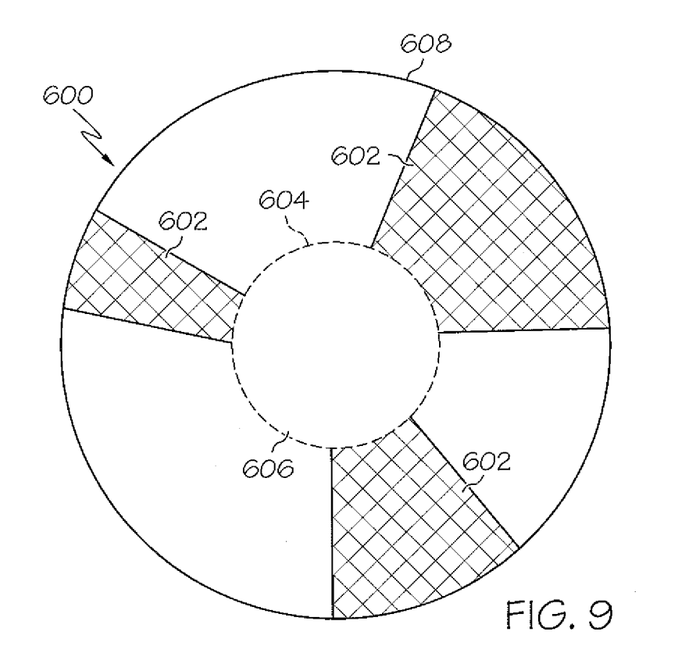

The specific stiffening pattern, depth profile, stiffening gradient (if any), and configuration of the stiffened regions can vary in many respects from patient to patient and from eye to eye. Moreover, in addition to the variations and options described above, a crystalline lens could be physically transformed such that its anterior surface region has a different stiffening pattern than its posterior surface region. FIGS. 7-9 are front views of crystalline lenses having different stiffening patterns resulting from in situ accommodation enhancement procedures. As described above with reference to FIG. 6, the stiffened regions depicted in FIGS. 7-9 could have a uniform or a non-uniform stiffness profile between the anterior and posterior regions of the crystalline lenses, depending upon the desired accommodation response. The stiffening patterns illustrated here are merely exemplary, and they are not intended to limit or restrict the application or scope of the described subject matter in any way.

FIG. 7 depicts a treated crystalline lens 400 having four stiffened peripheral regions 402. Each of the stiffened peripheral regions 402 is arc-shaped, and each extends to the outer circular perimeter 404 of the crystalline lens 400. The peripheral regions 402 are discontinuous around the circular perimeter 404. In other words, the crystalline lens 400 includes gaps 406 between adjacent peripheral regions 402. These gaps 406 allow the peripheral regions 402 to effectively transfer forces to the center region 4408 of the crystalline lens 400, which promotes accommodation. In contrast, if the peripheral regions 402 formed a continuous ring around the circular perimeter 404, then the ring would actually impede accommodation. Again, the shape, size, arrangement, and number of stiffened peripheral regions 402 might vary from one crystalline lens to another, depending upon the desired treatment plan.

FIG. 8 depicts a treated crystalline lens 500 having four asymmetrically arranged stiffened spokes 502. Each of the stiffened spokes 502 runs longitudinally from the imaginary boundary 504 of the center region 506 to the outer circular perimeter 508 of the crystalline lens 500. In contrast to the symmetrical arrangement of spokes 302 shown in FIG. 5, the crystalline lens 500 includes three spokes 502 near the top and only one spoke 502 at the bottom. This particular arrangement (which is merely exemplary) could be created to promote an asymmetric and/or non-uniform accommodative response in the presence of ciliary muscle forces. As mentioned previously, the shape, size, arrangement, and number of stiffened spokes 502 might vary from one crystalline lens to another, depending upon the desired treatment plan.

FIG. 9 depicts yet another treated crystalline lens 600 having three asymmetrically arranged stiffened spokes 602. Each of the stiffened spokes 602 runs longitudinally from the imaginary boundary 604 of the center region 606 to the outer circular perimeter 608 of the crystalline lens 600. In contrast to the symmetrical arrangement of spokes 302 shown in FIG. 5, the crystalline lens 600 includes three spokes 602 that are asymmetrically arranged. Moreover, each of the spokes 602 has a different shape and size. This particular arrangement (which is merely exemplary) could be created to promote an asymmetric and/or non-uniform accommodative response in the presence of ciliary muscle forces. Once again, the shape, size, arrangement, and number of stiffened spokes 602 might vary from one crystalline lens to another, depending upon the desired treatment plan.

Referring back to FIG. 4, if the capsular bag is to be treated (query task 216), then the lens treatment process 200 proceeds by increasing the stiffness of the specified treatment regions of the capsular bag (task 218). If the capsular bag is not to be treated, then the lens treatment process 200 may exit. In certain procedures, rather than ending at this point, the lens treatment process 200 continues by performing tasks related to other procedures related to the patient's eye, including, without limitation, laser-assisted in situ keratomileusis (LASIK). In practice, the capsular bag can be treated to form a desired pattern or layout of stiffened regions, sections, spaces, or volumes. Indeed, any one or combination of the characteristics of the crystalline lens stiffening patterns described above may also apply to the stiffening pattern created in the capsular bag or a portion of it. Accordingly, the entire capsular bag could be stiffened, selected portions (such as the outer periphery) of the capsular bag could be stiffened, stiffening features could be formed in the capsular bag tissue, etc.

The particular layout, geometry, arrangement, orientation, shape, size, and/or number of stiffened regions formed on the crystalline lens (and/or the capsular bag) can vary to allow for greater transfer of forces from the ciliary muscle to the capsular bag and, ultimately, to the crystalline lens itself. The embodiments described here use stiffened regions at or near the peripheral region of the natural lens because the ciliary muscle naturally pushes and pulls at the peripheral region. Consequently, the stiffened peripheral regions efficiently and effectively transfer ciliary muscle forces to the center region of the crystalline lens, thus amplifying the power change of the natural lens. After treatment, there will be a greater coupling of these forces to the anterior and/or posterior surfaces of the crystalline lens, resulting in more distortion or deforming of these surfaces for a given ciliary muscle force. As a result, the applied ciliary muscle force produce a greater deformation of the crystalline lens, and, therefore, a larger change in power and/or a larger axial translation of the image at the retina. In certain embodiments, the stiffened regions can be formed asymmetrically relative to the depth dimension of the natural lens. A potential advantage of such asymmetry is that the deformation of the anterior and posterior surface regions of the crystalline lens can be tailored more specifically than with a symmetric profile, so that one surface may deform more than the other under a deforming force exerted by the ciliary muscle. This may be desirable to produce desired optical effects for some patients.

The lens treatment process 200 can leverage one or more stiffening techniques, technologies, or procedures to stiffen the crystalline lens and/or the capsular bag. For example, one or more mechanical properties of the crystalline lens could be transformed and changed in accordance with one or more of the following techniques, without limitation: (1) by applying electromagnetic radiation to the crystalline lens treatment areas; (2) by applying a bio-adhesive agent to the crystalline lens treatment areas; (3) bio-welding the lens treatment areas; (4) by introducing a cross-linking agent to the crystalline lens treatment areas to cross-link proteins in the treatment areas; and (5) by introducing a stiffening agent to the crystalline lens treatment areas to stiffen cytoskeleton structure in the treatment areas.

If electromagnetic radiation is used, then the crystalline lens can be treated in a noninvasive manner without creating an incision or otherwise penetrating the cornea. Electromagnetic radiation can be selectively applied to certain designated sections of the crystalline lens such that those designated sections become stiffer. The electromagnetic radiation may be, without limitation: laser radiation; microwave radiation; ultraviolet radiation; infrared radiation; radiofrequency radiation; x-ray radiation; or gamma ray radiation. The controlled application of electromagnetic radiation in this manner increases the modulus of elasticity of the treated sections of the crystalline lens. In practice, the electromagnetic radiation could be selectively and precisely focused to create the desired pattern and layout of stiffened treatment areas. If certain wavelengths of electromagnetic radiation are used (e.g., visible light), then it may be possible to selectively mask the radiating waves into a desired pattern using, for example, photolithography techniques. Moreover, some types of electromagnetic radiation, such as laser radiation, can pass through the iris of the eye (which makes the stiffening treatment easier). As one example, microwave radiation could be used to harden sections of the crystalline lens, as mentioned in Pandey et al., *Creating Cataracts of Varying Hardness to Practice Extracapsular Cataract Extraction and Phacoemulsification*, Journal of Cataract & Refractive Surgery, Volume 26, Pages 322-329 (2000), and in Pau, *Cortical and Subcapsular Cataracts: Significance of Physical Forces*, Ophthalmologica, Volume 220, Pages 1-5 (2006). The content of these papers is incorporated by reference herein. The desired increase in stiffness, the depth of the stiffened regions, and possibly other characteristics of the stiffened treatment regions can be controlled by adjusting the amount of energy delivered by the electromagnetic radiation source, by adjusting the parameters of the electromagnetic energy pulses (e.g., pulse width, duty cycle, pulse frequency, pulse intensity), by adjusting the wavelength of the electromagnetic radiation, etc. One or more of these parameters could also be controlled or adjusted to reduce the amount of heat generated during the procedure.

In certain embodiments, bio-adhesive and/or bio-welding techniques can be used to stiffen the designated sections of the crystalline lens. In this context, a bio-adhesive adhesive or a bio-welding agent is any chemical, compound, substance, material, or composition that can be physically applied to a treatment area to stiffen, harden, or mechanically reinforce that treatment area. Moreover, any bio-adhesive or bio-welding agent used for this purpose should be biocompatible and biologically tolerable. To stiffen an area of the crystalline lens, a bio-adhesive or bio-welding agent can be physically applied to the desired treatment areas using, for example, an applicator, a brush, a syringe, or the like. A bio-adhesive agent adheres to the cells in the crystalline lens and cures or hardens in situ. Thus, a bio-adhesive agent can be "painted" or applied selectively onto the crystalline lens in the desired stiffening pattern. One suitable bio-adhesive agent that can be used to stiffen the crystalline lens is cyanoacrylate surgical adhesive. Other suitable bio-adhesive agents include, without limitation: fibrin adhesive; polymerizing liquid hydrogel (PEG hydrogel); protein glue; or possibly other wound closure materials. One application for a liquid hydrogel is discussed in Hovanesian, *Cataract Wound Closure with a Polymerizing Liquid Hydrogel Ocular Bandage*, Journal of Cataract & Refractive Surgery, Volume 35, Pages 912-916 (2009), the content of which is incorporated by reference herein. One application for a fibrin tissue adhesive is discussed in Hovanesian et al., *Watertight Cataract Incision Closure Using Fibrin Tissue Adhesive*, Journal of Cataract & Refractive Surgery, Volume 33, Pages 1461-1463 (2007), the content of which is incorporated by reference herein. An example of a bio-welding process is laser-induced sealing of tissue based on direct absorption of infrared laser light with topical application of indocyanine green (ICG) dye to the tissue. One laser welding technique is discussed in Menabuoni et al., *Laser-Assisted Corneal Welding in Cataract Surgery: Retrospective Study*, Journal of Cataract & Refractive Surgery, Volume 33, Pages 1608-1612 (2007), the content of which is incorporated by reference herein.

In some embodiments, chemical agents or compounds can be used to stiffen certain portions of the crystalline lens. For instance, self-hardening chemical agents could be used to harden sections of the crystalline lens, as mentioned in U.S. Pat. No. 6,887,083 (which is incorporated by reference herein). As another example, a cross-linking agent could be used to cross-link (and, therefore, stiffen) proteins in the treatment areas of the crystalline lens. Suitable collagen cross-linking agents include, without limitation: riboflavin and ultraviolet-A (UVA) light. In certain embodiments, a photosensitizing agent such as riboflavin can be applied to the treatment areas, and the photosensitized treatment areas can thereafter be subjected to ultraviolet radiation to cross-link the treatment areas. Cross-linking could also be achieved using different approaches. For example, glutaraldehyde-induced crosslinking, hydrogen peroxide, glycation by glucose and/or ascorbate could be utilized. One photochemical crosslinking technique is discussed in Chan et al., *Effects of Photochemical Crosslinking on the Microstructure of Collagen and a Feasibility Study on Controlled Protein Release*, Acta Biomaterialia 4, Pages 1627-1636 (2008), the content of which is incorporated by reference herein.

In yet other embodiments, chemical agents or compounds can be used to stiffen the cytoskeleton structure in the treatment areas (cytoskeleton refers to microfilaments, thought to be actin, resident in the crystalline lens fiber cells). This approach is similar to the protein cross-linking approach described above, but the cytoskeleton of the cells is stiffened rather than the collagen. Stiffening agents that harden the cytoskeleton include, without limitation: actinin and fascin. The use of such actin-crosslinking proteins is discussed by Tseng et al. in *How Actin Crosslinking and Bundling Proteins Cooperate to Generate an Enhanced Cell Mechanical Response*, Biochemical and Biophysical Research Communications 334, Pages 183-192 (2005). The content of this paper is incorporated by reference herein.

It may be possible to stiffen designated treatment areas of the capsular bag using one or more of the techniques, technologies, or procedures described above for stiffening of the crystalline lens. One technique particularly suited for stiffening the capsular bag involves the application of riboflavin (using, for example, a syringe) to make sections of the capsular bag photosensitive. Thereafter, the photosensitive sections of the capsular bag are exposed to ultraviolet light while other parts of the eye are masked or otherwise protected, which cross-links collagen in the capsular bag.

Figure 10:
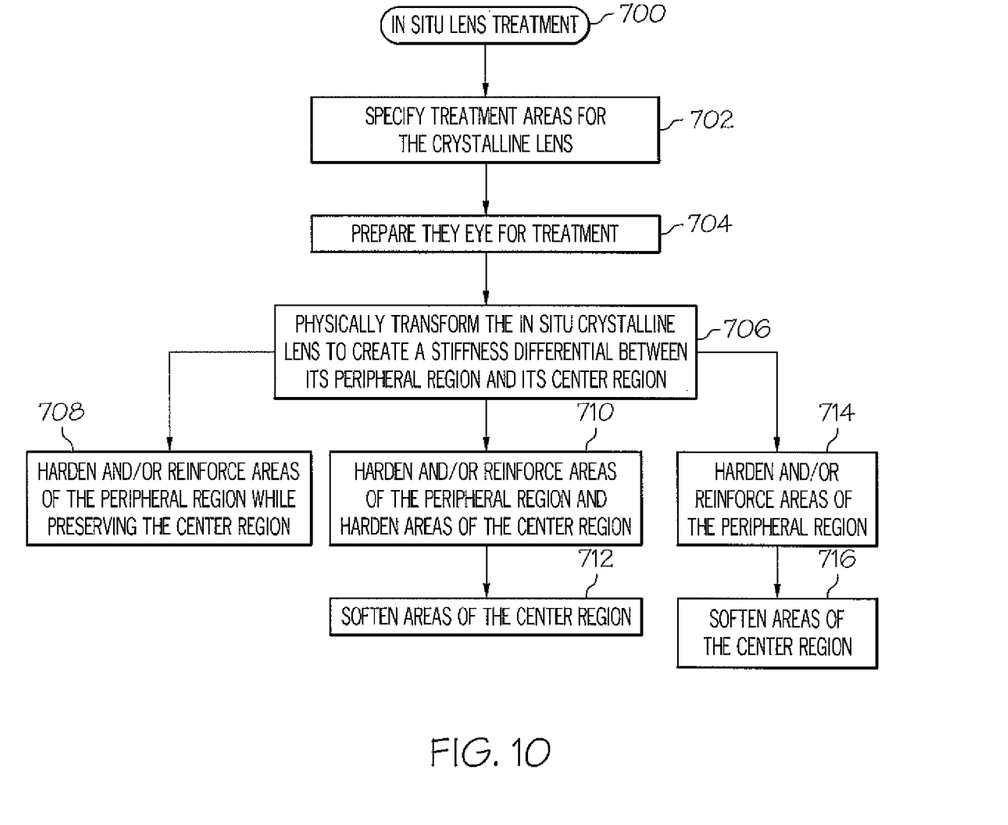

The lens treatment process 200 described above represents one simplified and generalized process that creates stiffened regions in the crystalline lens and/or the capsular bag. Alternatively, some regions of the natural lens could be stiffened while other regions are softened or otherwise made more pliable or flexible. In this regard, FIG. 10 is a flow chart that illustrates another exemplary embodiment of an in situ lens treatment process 700. It should be appreciated that the lens treatment process 700 may include any number of additional or alternative tasks, the tasks shown in FIG. 10 need not be performed in the illustrated order, and that the lens treatment process 700 may be incorporated into a more comprehensive procedure or process having additional tasks that are not described in detail herein. Moreover, one or more of the illustrated tasks of the lens treatment process 700 may be optional in nature and, therefore, such optional tasks could be omitted.

The lens treatment process 700 may begin by specifying or designating certain treatment areas of the natural lens (task 702), as described above for task 202 of the lens treatment process 200. Although the specified treatment areas might correspond to treatment regions of the capsular bag and/or treatment regions of the crystalline lens, this embodiment assumes that only the crystalline lens is treated. After planning and specifying the desired treatment areas, the patient and the eye can be prepared for the treatment procedure (task 704), as described above for task 204 of the lens treatment process 200.

The lens treatment process 700 treats the natural lens of the eye by physically transforming, modifying, altering, and/or supplementing at least a portion of the crystalline lens while it remains in situ. The physical transformation is performed to create a stiffness differential between the peripheral region and the center region of the crystalline lens (task 706). As a result of this physical transformation, at least a portion of the peripheral region of the crystalline lens is stiffer than the center region of the crystalline lens. Although the characteristics of the stiffness differential may vary from one patient to another (and from one eye to another), in certain embodiments the peripheral region is at least about two times stiffer than the center region after treatment. The lens treatment process 700 contemplates at least three different methodologies for creating the stiffness differential. Accordingly, task 706 leads to three different branches in the illustrated flow chart.

In certain situations, it may be desirable to harden and/or reinforce the peripheral region of the crystalline lens while preserving most if not all of the center region of the crystalline lens (task 708). This situation corresponds to that described above with reference to the lens treatment process 200. Stiffening of the peripheral region of the crystalline lens in this manner creates a stiffness differential that enhances the transfer of ciliary muscle forces from the peripheral region to the center region of the crystalline lens. The peripheral region of the crystalline lens can be hardened or mechanically reinforced using any of the techniques, methodologies, and procedures described above for the lens treatment process 200.

In some situations, the stiffness differential in the crystalline lens could be achieved by softening some or all areas of the center region of the crystalline lens. In one exemplary procedure, the lens treatment process 700 hardens and/or reinforces certain areas of both the peripheral region and the center region of the crystalline lens (task 710), and thereafter softens designated areas of the center region (task 712). For task 710, the peripheral and center regions of the crystalline lens could be hardened or reinforced using any of the techniques, methodologies, and procedures described above for the lens treatment process 200. For this variation of the lens treatment process 700, the center region of the crystalline lens is softened to further enhance the transfer of ciliary muscle forces from the peripheral region to the center region of the crystalline lens. For task 712, the center region of the crystalline lens is softened using any suitable technique, procedure, or methodology. For example, electromagnetic radiation having appropriate characteristics could be applied to the center region in a controlled manner to soften it and, therefore, improve its ability to accommodate. The center region could be softened to achieve its pre-treatment modulus of elasticity, or to obtain a modulus that is less than its pre-treatment modulus.

In another exemplary variation of the lens treatment process 700, the peripheral region of the crystalline lens is hardened and/or reinforced (task 714) using any of the techniques, methodologies, or procedures described above for the lens treatment process 200. In addition to the stiffening of the peripheral region, this variation of the lens treatment process 700 softens areas of the center region of the crystalline lens (task 716) using any of the techniques, methodologies, or procedures described previously for task 712. In contrast to the second variation of the lens treatment process 700 (which hardens or reinforces both the peripheral and center regions of the crystalline lens), this third variation hardens only the peripheral region of the crystalline lens. Consequently, task 716 is performed to make the center region softer than its pre-treatment condition. Thus, the lens treatment process 700 creates the stiffness differential in the crystalline lens by hardening/reinforcing the outer region of the crystalline lens while also softening the center region of the crystalline lens.

For some procedures, the lens treatment process 700 may soften some designated portions, sections, or areas of the peripheral region of the crystalline lens. Such softening of the peripheral region could be combined with the stiffening of other areas of the peripheral region. In other words, a first portion of the peripheral region can be stiffened while a second portion of the peripheral region is either softened or left untreated. Such a treatment may produce anisotropic stiffening characteristics, as discussed above. Moreover, such softening of the peripheral region could be performed in conjunction with (or as an alternative to) any of the three exemplary approached described above for the lens treatment process 700.

Figure 11:
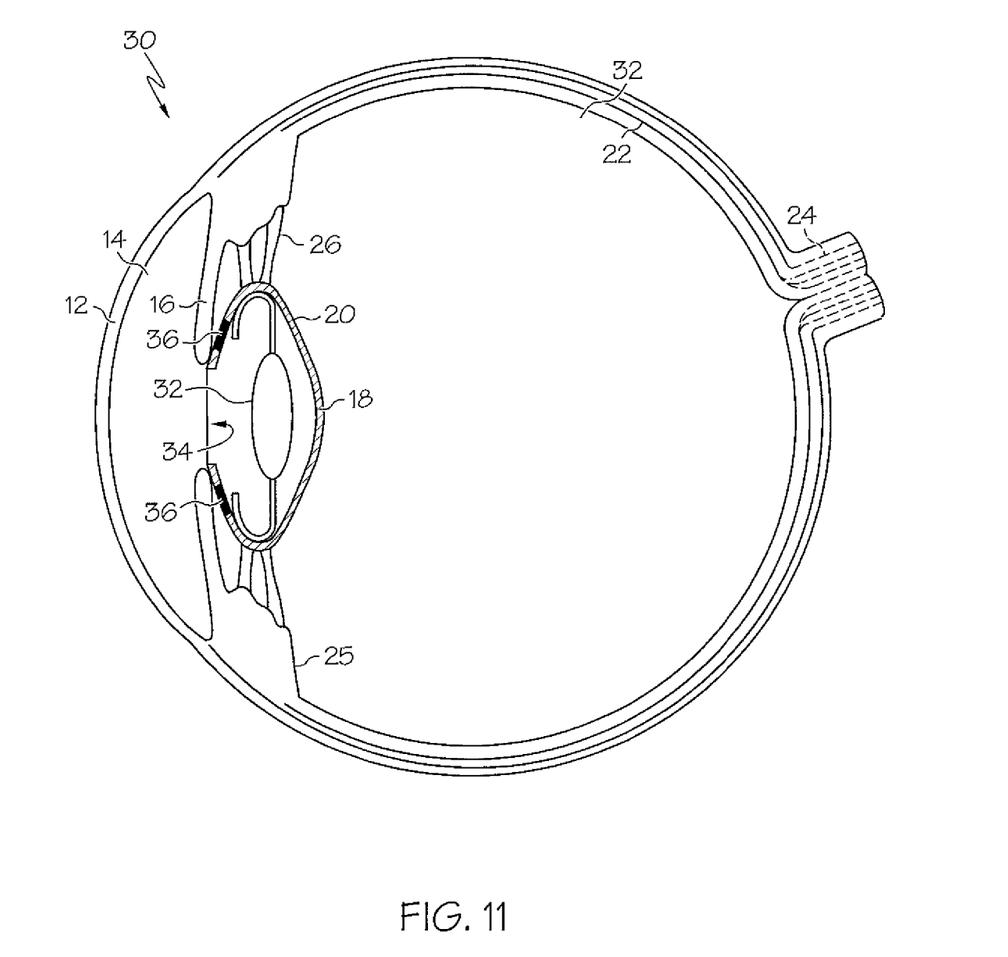

As described above with reference to the lens treatment process 200 (FIG. 4), it may be desirable to stiffen the capsular bag to improve the accommodation properties of the natural eye. However, the stiffening procedures described above could also be utilized to stiffen portions or regions of the capsular bag before and/or after the crystalline lens has been removed and an IOL inserted into the capsular bag. In this regard, FIG. 11 is a cross-sectional diagram of a human eye 30 with an IOL 32 residing in the capsular bag 18. FIG. 11 is very similar to FIG. 1, and common reference numbering is used in both figures to refer to the same or equivalent structures. In contrast to that depicted in FIG. 1, the crystalline lens of the eye 30 has been removed and replaced with the IOL 32. Capsulorhexis can be utilized to form an opening 34 in the capsular bag 18 to facilitate removal of the crystalline lens and insertion of the IOL 32. Techniques and procedures related to the insertion of IOLs are well known and will not be described in detail here. In some embodiments, the capsular bag is stiffened and/or otherwise treated, for example, to increase the integrity of the capsular bag for increasing the range of accommodation provided by and accommodating IOL or an injectable lens. For example, the region of the capsular bag adjacent the capsulorhexis is stiffened and/or otherwise treated to increase its stiffness, strength, or other mechanical characteristics of the region about the capsulorhexis. In some embodiments, treatment of regions adjacent the capsulorhexis, or other portions of the capsular bag, may include insertion and/or attachment of a device to the capsular bag, for example, an annular device disposed along the capsulorhexis and/or a transparent device located over the opening created by the capsulorhexis.

In this example, the capsular bag 18 has been treated to form a stiffening ring 36 on its anterior surface. In FIG. 11, the stiffening ring 36 is depicted in cross-section as two darkened blocks, although in reality the stiffening ring 36 will form a continuous path around the opening 34. The stiffening ring 36 could be formed prior to removal of the crystalline lens or after insertion of the IOL 32. Alternatively, the stiffening ring 36 or portions thereof could be formed by treating the capsular bag 18 both before and after placement of the IOL 32. The stiffening ring 36 will enhance the transfer of ciliary muscle forces to the IOL 32, in accordance with the same mechanical principles discussed above. Thus, the stiffening ring 36 will improve the accommodative properties of the IOL 32.

Although FIG. 11 depicts an eye 30 where a simple stiffening ring 36 has been created, other stiffening features can be formed in the capsular bag 18. For instance, as mentioned previously, the specific shape, size, arrangement, pattern, orientation, and/or dimensions of the stiffening feature(s), member(s), and/or ring(s) formed in or on the capsular bag 18 may vary from one patient to another. The particular stiffening ring 36 depicted in FIG. 11 is not intended to limit or otherwise restrict the scope of this embodiment.

While at least one exemplary embodiment has been presented in the foregoing detailed description, it should be appreciated that a vast number of variations exist. Moreover, any of the techniques and procedures described above could be used in combination with other enhancements to the natural lens and/or the cornea. Furthermore, some of the techniques and procedures described above could be used in combination with a phakic intraocular lens, and some of the techniques and methodologies described above could be used in combination with intracorneal inlays. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of enhancing accommodative properties of an eye, the eye comprising a capsular bag and a lens inside the capsular bag, the method comprising:
   identifying treatment areas corresponding to regions of the capsular bag or regions of the lens; and
   increasing stiffness of the treatment areas; wherein the increasing step is selected from the group consisting of: applying a bio-adhesive agent to the treatment areas; introducing a cross-linking agent to the treatment areas; and introducing a stiffening agent to the treatment areas.

2. The method of claim 1, wherein increasing stiffness of the treatment areas results in stiffened areas of the lens that enhance transfer of ciliary muscle forces to a center region of the crystalline lens.

3. The method of claim 1, further comprising specifying treatment areas for both the capsular bag and the lens, wherein the increasing step increases the stiffness of the treatment areas for both the capsular bag and the lens.

4. The method of claim 1, further comprising specifying treatment areas of the capsular bag only, wherein the increasing step increases the stiffness of the treatment areas of the capsular bag only.

5. The method of claim 1, further comprising specifying treatment areas of the lens only, wherein the increasing step increases the stiffness of the treatment areas of the lens only.

6. The method of claim 1, further comprising specifying treatment areas corresponding to peripheral regions of the lens.

7. The method of claim 1, further comprising specifying treatment areas corresponding to peripheral regions of the capsular bag.

8. A method for treating a natural lens of an eye, the natural lens comprising a crystalline lens that accommodates in response to ciliary muscle forces, wherein the method comprises increasing stiffness of regions of the crystalline lens while the crystalline lens remains in situ; wherein the increasing step is selected from the group consisting of: applying a bio-adhesive agent to the treatment areas; introducing a cross-linking agent to the treatment areas; and
   introducing a stiffening agent to the treatment areas.

9. The method of claim 8, further comprising increasing peripheral regions of the crystalline lens.

10. The method of claim 8, further comprising increasing the modulus of elasticity of peripheral regions of the crystalline lens.

11. The method of claim 8, further comprising increasing the stiffness of peripheral regions of the crystalline lens in accordance with a predetermined stiffening pattern.

12. The method of claim 11, wherein the predetermined stiffening pattern defines a plurality of radial stiffening spokes for the peripheral regions of the crystalline lens.

13. The method of claim 8, further comprising softening a center region of the crystalline lens to enhance transfer of ciliary muscle forces from peripheral regions of the crystalline lens to the center region of the crystalline lens.

14. The method of claim 8, further comprising softening at least a portion of peripheral regions of the crystalline lens.

15. The method of claim 8, further comprising creating a non-uniform stiffness profile between an anterior surface region and a posterior surface region of the crystalline lens.

16. The method of claim 8, further comprising creating a stiffness gradient between an anterior surface region and a posterior surface region of the crystalline lens.

17. The method of claim 8, further comprising creating a stiffness gradient between a center region of the crystalline lens and peripheral regions of the crystalline lens.

18. The method of claim 8, wherein the increasing step creates stiffened areas that are arranged and oriented to introduce non-uniform optical power change for the anterior and posterior surfaces of the crystalline lens.

19. The method of claim 8, wherein the increasing step creates stiffened areas that are arranged to reduce one or more optical aberrations of the natural lens of the eye.

20. The method of claim 19, wherein the optical aberrations are selected from the group consisting of: spherical aberration; coma; and astigmatism.

21. The method of claim 8, wherein the increasing step creates stiffened areas that are arranged to modify an optical power of the natural lens of the eye.

22. The method of claim 8, wherein the increasing step creates stiffened areas that are arranged to provide a plurality of focal lengths for the natural lens of the eye.

23. A method of restoring accommodative characteristics of a natural lens of an eye, the natural lens comprising a crystalline lens that mechanically responds to ciliary muscle forces applied thereto, the method comprising physically transforming the crystalline lens, while it remains in situ, to create a stiffness differential between at least a portion of a peripheral region of the crystalline lens and a center region of the crystalline lens, wherein the at least a portion of the peripheral region of the crystalline lens is stiffer than the center region of the crystalline lens; wherein the creation of the stiffness differential is selected from the group consisting of: applying a bio-adhesive agent to the treatment areas; introducing a cross-linking agent to the treatment areas; and introducing a stiffening agent to the treatment areas.

24. The method of claim 23, wherein the step of physically transforming the crystalline lens comprises hardening at least a portion of the peripheral region of the crystalline lens to enhance transfer of ciliary muscle forces from the peripheral region of the crystalline lens to the center region of the crystalline lens.

25. The method of claim 23, wherein the step of physically transforming the crystalline lens further comprises softening the center region of the crystalline lens to further enhance transfer of ciliary muscle forces from the peripheral region of the crystalline lens to the center region of the crystalline lens.

26. The method of claim 23, wherein the step of physically transforming the crystalline lens comprises mechanically reinforcing at least a portion of the peripheral region of the crystalline lens to enhance transfer of ciliary muscle forces from the peripheral region of the crystalline lens to the center region of the crystalline lens.

27. The method of claim 23, wherein the step of physically transforming the crystalline lens comprises:
   hardening at least a portion of the peripheral region of the crystalline lens and the center region of the crystalline lens; and
   thereafter, softening the center region of the crystalline lens to enhance transfer of ciliary muscle forces from the peripheral region of the crystalline lens to the center region of the crystalline lens.

* * * * *